(12) United States Patent
Miller et al.

(10) Patent No.: US 7,358,414 B2
(45) Date of Patent: Apr. 15, 2008

(54) PARA-XYLENE PROCESS USING PERM-SELECTIVE SEPARATIONS

(76) Inventors: Jeffrey T. Miller, 2039 Springside Dr., Naperville, IL (US) 60563; Bo Chen, 816 Corday Dr., Apt. 105, Naperville, IL (US) 60540; Craig W. Colling, 3S 710 River Rd., Warrenville, IL (US) 60555; George A. Huff, Jr., 823 Morven Ct., Naperville, IL (US) 60563; Marvin L. Cadwell, 28W046 Countryview Dr., Naperville, IL (US) 60564

( * ) Notice: Subject to any disclaimer, the term of this patent is extended or adjusted under 35 U.S.C. 154(b) by 679 days.

(21) Appl. No.: 10/769,538

(22) Filed: Jan. 30, 2004

(65) Prior Publication Data

US 2005/0167338 A1   Aug. 4, 2005

(51) Int. Cl.
  *C07C 7/144* (2006.01)
(52) U.S. Cl. ............ 585/805; 585/818; 585/819; 585/478; 585/481; 585/321
(58) Field of Classification Search .......... 585/805, 585/819, 477, 478, 481, 321
See application file for complete search history.

(56) References Cited

U.S. PATENT DOCUMENTS

| | | | | |
|---|---|---|---|---|
| 3,299,157 A | | 1/1967 | Baddour et al. | 260/674 |
| 4,326,092 A | * | 4/1982 | Neuzil | 585/828 |
| 4,638,105 A | | 1/1987 | Chang et al. | 585/481 |
| 4,743,708 A | | 5/1988 | Rosenfeld et al. | 585/828 |
| 4,758,348 A | * | 7/1988 | Matsui et al. | 210/651 |
| 4,886,929 A | | 12/1989 | Neuzil et al. | 585/828 |
| 4,899,011 A | | 2/1990 | Chu et al. | 585/481 |
| 4,899,017 A | | 2/1990 | Yan | 585/481 |
| 4,925,459 A | | 5/1990 | Rojey et al. | 95/50 |
| 4,940,830 A | | 7/1990 | Zinner et al. | 585/812 |
| 5,004,860 A | | 4/1991 | Hansen et al. | 585/812 |
| 5,169,530 A | | 12/1992 | Schucker et al. | 210/321.81 |
| 5,171,922 A | | 12/1992 | Anderson | 585/805 |
| 5,177,295 A | | 1/1993 | Oroskar et al. | 585/605 |
| 5,208,316 A | * | 5/1993 | Yoshinaga | 528/68 |
| 5,329,060 A | | 7/1994 | Swift | 585/805 |

(Continued)

FOREIGN PATENT DOCUMENTS

WO   WO9727159   7/1997

OTHER PUBLICATIONS

Chen et al. "PVA membrane filled beta-cyclodextrin for separation of isomeric xylenes by pervaporation", 2000, vol. 78, pp. 159-164.*

(Continued)

*Primary Examiner*—Tam M. Nguyen
(74) *Attorney, Agent, or Firm*—Thomas A. Yassen

(57) ABSTRACT

Processes and apparatus are disclosed for recovery of purified products from a fluid mixture by means of integrated perm-selective separations with purified product recovery operations. More particularly, integrated processes of the invention comprise separations by means of one or more devices using polymeric membranes coupled with recovery of purified products by means of fractional crystallization and/or selective sorption. Processes of the invention are particularly useful for recovery of a very pure aromatic isomer when processing aromatic starting materials, for example, a pure para-xylene product from liquid mixtures even containing ethylbenzene as well as the three xylene isomers.

8 Claims, 2 Drawing Sheets

U.S. PATENT DOCUMENTS

| | | | |
|---|---|---|---|
| 5,352,361 A | 10/1994 | Pragad et al. | 210/321.61 |
| 5,382,747 A | 1/1995 | Kulprathipanja | 585/828 |
| 5,470,469 A | 11/1995 | Eckman | 210/321.8 |
| 5,495,061 A | 2/1996 | Kulprathipanja | 585/828 |
| 5,498,822 A | 3/1996 | Eccli et al. | 585/816 |
| 5,866,740 A | 2/1999 | Mikitenko et al. | 585/470 |
| 5,942,119 A | 8/1999 | Deckman et al. | 210/651 |
| 6,111,161 A | 8/2000 | MacPherson et al. | 585/812 |
| 6,137,024 A | 10/2000 | Zinnen et al. | 585/828 |
| 6,147,272 A | 11/2000 | Mikitenko et al. | 585/812 |
| 6,194,609 B1 | 2/2001 | Abrams et al. | 562/486 |
| 6,376,733 B1 | 4/2002 | Ferraro et al. | 585/805 |
| 6,500,233 B1 | 12/2002 | Miller et al. | 95/50 |

OTHER PUBLICATIONS

Kusumocahyo et al. "Pervaporation of xylene isomer mixture through cyclodextrins containing polyacrylic acid membranes", Journal of Membrane Science, vol. 231, issues 1-2, Mar. 1, 2004, pp. 127-132.*

* cited by examiner

PARA-XYLENE PROCESS USING PERM-SELECTIVE SEPARATIONS

TECHNICAL FIELD

The present invention relates to processes for recovery of purified products from a fluid mixture by means of integrated perm-selective separations with purified product recovery operations. More particularly, integrated processes of the invention comprise separations by means of one or more devices using polymeric perm-selective membranes coupled with recovery of purified products by means of fractional crystallization and/or selective sorption. Processes of the invention are particularly useful for recovery of a very pure aromatic isomer when processing aromatic starting materials, for example, a pure para-xylene product from liquid mixtures even containing ethylbenzene as well as the three xylene isomers.

BACKGROUND OF THE INVENTION

The $C_8$ aromatics exist as ethylbenzene and three isomers of xylene (dimethylbenzenes) which are separated only with great difficulty because they have boiling points which are very close together. Para-xylene is used in the manufacture of terephthalic acid which in turn is subsequently employed in the manufacture of various synthetic fibers, such as polyester. Meta-xylene is used for the manufacture of insecticides, isophthalic acid or alkyd resins. Ortho-xylene can be used as material for plasticizers. Benzene di- and tri-carboxylic acids have wide industrial application including the manufacture of polyesters, polyamides, and fibers and films. For commercial manufacture of these products the required source of high purity benzene di- and tri-carboxylic acids may be obtained from a corresponding substituted aromatic compound by catalytic oxidation of methyl moieties to carboxylic acid moieties, advantageously in a liquid-phase medium.

The possibility of utilizing a liquid-phase instead of vapor-phase oxidation for the preparation of benzene carboxylic acids was first indicated by the disclosure in U.S. Pat. No. 2,245,528 of the catalysis provided by variable valence metals, especially cobalt, in a liquid-phase of saturated lower aliphatic acid at elevated temperature and pressures to maintain the liquid phase of the aliphatic acid. Combinations of cobalt and manganese with a source of bromine have become preferred for commercial use, for example, see U.S. Pat. No. 2,833,816. A key element in obtaining benzene di- and tri-carboxylic acids having suitable high purity for these oxidation processes is using an oxidation feedstock of high purity.

Various commercial processes for separation of para-xylene from $C_8$ aromatics have been developed as alternatives to fractional distillation. Such processes utilize either differences of the freezing points between ethylbenzene, ortho-xylene, meta-xylene and para-xylene, (fractional crystallization) and/or processes based upon properties of zeolite materials to selectively adsorb para-xylene from mixtures of $C_8$ aromatics; the adsorbed paraxylene is recovered after desorbing from the zeolite.

Either of these processes can recover paraxylene in high yields from available mixtures of $C_8$ aromatics. However, they involve reprocessing large amounts of the resulting filtrate from the crystallization process or the raffinate from the adsorption process. These streams are depleted in paraxylene and contain relatively high proportions of ethylbenzene, ortho-xylene, and meta-xylene. Furthermore, these streams are typically subjected to further processing downstream of the crystallization or adsorption process.

Crystallization methods have been used in commercial processes to separate para-xylene from aromatic starting materials containing ethylbenzene as well as the three xylene isomers. Use is made of the fact that melting point temperatures of the individual isomers of xylene are significantly different. Ortho-xylene has a freezing point of negative 25.2° C., meta-xylene has a freezing point of negative 47.9° C. and para-xylene has a freezing point of 13.3° C. However, conventional crystallization methods can be used to make para-xylene with a purity of 99.8 percent by weight only with great expense.

Crystallization processes to recover para-xylene from a mixture of $C_8$ aromatics requires cooling a feed stream, for example an equilibrium mixture of isomers from reformate and/or xylene isomerization processes. Because it's melting point is much higher than that of other $C_8$ aromatics, para-xylene crystals are readily formed in a crystallizer after refrigeration of the feed solution. Feed mixtures of refinery aromatic streams typically contain about 22 to about 23 percent by weight of para-xylene. In order to crystallize a substantial amount of the para-xylene from solution, the solution has to be cooled to just above the eutectic temperature (i.e. the temperature at which a second component start to co-crystallize and contaminate the para-xylene crystals). The eutectic temperature is determined by the composition of the remaining mother liquor after para-xylene crystals are removed from the mixture (mostly meta-xylene, ortho-xylene and ethylbenzene). Although not known with absolute certainty, it is believed that the eutectic temperature decreases with higher relative composition of ethylbenzene in the remaining mother liquor. As the eutectic temperature decreases, the concentration of para-xylene in the outlet stream also decreases, increasing the para-xylene recovery. Given a mixture of xylenes with relative ratio of para-xylene:meta-xylene:ortho-xylene:ethylbenzene of about 2:4:2:1, at temperatures within about 3° to 6° C. of the eutectic temperature the para-xylene recovery is limited to about 70 percent.

Typically a reject stream depleted in para-xylene, but containing relatively high proportions of ethylbenzene, ortho-xylene, and meta-xylene from the crystallization process or the adsorption processes, are treated in an isomerization process which is used to increase the proportion of para-xylene in para-xylene depleted streams. The para-xylene depleted stream can be contacted with an isomerization catalyst under appropriate temperature and pressure which results in the conversion of some of the ortho-xylene and meta-xylene to para-xylene. It is also usually desirable to convert some of the ethylbenzene to prevent it from building up to high concentrations. Known catalysts are selected to enable conversion of ethylbenzene to benzene and ethane via hydro dealkylation, and/or $C_8$ isomerization to an equilibrium mixture of xylenes.

Processes for making para-xylene therefore included combinations of isomerization with fractional crystallization and/or adsorption separation. The disadvantage with such combinations is that, despite improvements in catalyst performance isomerization technology is only able to produce equilibrium or near-equilibrium mixtures of the xylene isomers and typically is also relatively inefficient for the conversion of ethylbenzene to benzene and/or isomers of xylene. Consequently big recycles of the reject streams back through these processes are needed to ensure the conversion of the $C_8$ aromatics stream to para-xylene is maximized with or without the additional recovery if desired of ortho-xylene and/or meta-xylene. There is a need therefore for improved processes and chemical plants for the production of para-xylene from mixtures of $C_8$ aromatics, which in particular address the problems associated with large recycles and/or low ethylbenzene conversions.

Accordingly, it is an object of the invention to overcome one or more of the problems described above.

A new approach to recovery of a very pure aromatic isomer has now been found when processing aromatic starting materials, for example, a pure para-xylene product from liquid mixtures containing ethylbenzene as well as the three xylene isomers. The new approach beneficially provides a process for recovering para-xylene having a purity of at least 99.5 percent by weight, and advantageously 99.8 percent from liquid mixtures of aromatic compounds, even containing ethylbenzene as well as the three xylene isomers.

As will be described in greater detail hereinafter, the present invention provides processes for recovery of purified products from a fluid mixture by means of an integrated fractional crystallization and perm-selective membrane separation apparatus. Integrated apparatus of the invention comprises a fractional crystallization unit coupled to one or more devices using polymeric membranes for recovery of purified products.

There is a need for a cost effective method of producing high purity para-xylene from a $C_8$ aromatic mixture containing para-xylene, meta-xylene, ortho-xylene and ethylbenzene which overcomes the aforementioned eutectic limit for crystallization.

SUMMARY OF THE INVENTION

In broad aspect, the present invention is directed to integrated processes that comprise separations by means of one or more devices using perm-selective membranes coupled with recovery of purified products by means of fractional crystallization and/or selective sorption. Processes of the invention are particularly useful for recovery of purified isomer of xylene when processing aromatic starting materials, for example, a very pure para-xylene product.

This invention contemplates the treatment of a fluid feedstock, e.g. various type organic materials, especially a fluid mixture of compounds of petroleum origin. In general, the fluid feedstock is a liquid mixture comprising a more selectively permeable component and a less permeable component.

Processes of the invention are particularly useful in processes for treatment of a mixture comprised of one or more products from reforming reactions, catalytic cracking reactions, hydro-processing reactions, para-selective toluene disproportion, a $C_6$ to $C_{10}$ aromatics trans-alkylation reaction, and/or methylation of benzene and/or toluene. For example, the invention provides integrated separation processes for recovering para-xylene from a fluid mixture comprising para-xylene and at least one other isomer of xylene, ethylbenzene or mixtures thereof.

In one aspect, the invention provides a process for recovering para-xylene from a fluid mixture of aromatic compounds which process comprises: (i) withdrawing from a perm-selective membrane device a first fluid stream having an enriched content of para-xylene compared to that of a second effluent stream which streams are derived by selective permeation of at least one aromatic compound from a fluid mixture of para-xylene with other aromatic compounds; and (ii) distributing all or portion of the first stream withdrawn from the membrane device into para-xylene concentration unit to extract therefrom a purified product having an enriched content of the para-xylene compared to that of first stream, and a reject stream as mother liquor product. Advantageously, the membrane device utilizes a perm-selective membrane comprising at least one polymeric material.

Where the desired purified product is an aromatic compound having 8 carbon atoms, the membrane device utilizes a plurality of perm-selective membranes which under a suitable differential of a driving force exhibit a permeability of at least 0.1 Barrer for at least one of the isomers of xylene or ethylbenzene.

Where purified para-xylene is also a desired product and the reject stream comprises ethylbenzene and a mixture of xylenes lean in at least para-xylene, processes of the invention advantageously further comprises; passing at least a portion of the reject stream to a catalytic conversion process to produce a stream having an enriched para-xylene content compared to that of the reject stream. Typically, the catalytic conversion process comprises contacting with a suitable isomerization catalyst under conditions of temperature, pressure, and time sufficient to produce an isomerate comprising an equilibrium mixture of xylenes. The isomerization catalyst beneficially comprises a zeolitic component and an acidic inorganic oxide support which has incorporated therewith at least one component comprising a metal selected from the group consisting of the transition elements in Group VIB and Group VIIIA of the Periodic Table of the Elements. Typically the isomerization catalysts comprise least one component comprising a metal selected from the group consisting of molybdenum, nickel, palladium and platinum. Advantageously the fluid mixture comprises at least a portion of the isomerate. Also at least a portion of the isomerate can be admixed with suitable products of reforming, hydro-processing, toluene disproportion, a $C_6$ to $C_{10}$ aromatics trans-alkylation, and/or methylation of benzene and/or toluene to form the fluid mixture.

In one aspect of the invention, the membrane device utilizes a perm-selective membrane which comprises: (i) a polymeric material, and (ii) embedded therein a plurality of granules comprising at least one natural and/or synthetic crystalline aluminosilicate. Advantageously, a perm-selective membrane comprises: a polymeric material and granules of an aluminosilicate which exhibits the MFI crystalline structure.

In another aspect of the invention the membrane device utilizes a perm-selective membrane which comprises: (i) a polymeric material, and (ii) incorporated therein a plurality of discrete components comprising at least one cyclodextrin. Advantageously, a perm-selective membrane comprises: a polymeric material and a plurality of discrete components comprising β-cyclodextrin or γ-cyclodextrin.

Membrane devices, particularly useful for purification of substituted aromatic compounds, utilize a perm-selective membrane comprising at least one polymeric material selected from the group consisting of polyamides, polyimides, poly(amide)imides, polyaramides, polyarylates, polytriazoles, polypyrrolone, polyurethane and copolymers thereof. Advantageously, the membrane device utilizes a perm-selective membrane comprising at least one polymeric material selected from the group consisting of polyamides, polyimides, and poly(amide)imides.

Processes in accordance with the invention integrate perm-selective separations with recovery of purified products by means of fractional crystallization and/or selective sorption. In processes for recovering a purified xylene from a fluid mixture of aromatic compounds according to the invention, concentration operations comprises a selective sorption purification. Beneficially, the selective sorption purification utilizes at least one natural and/or synthetic crystalline aluminosilicate, Y-type zeolite and/or X-type zeolite.

In yet another aspect of processes according to the invention the para-xylene concentration comprises a fractional crystallization step. Beneficially such para-xylene concentration further comprises a selective sorption of at least para-xylene from a fluid mixture of para-xylene and other aromatic compounds containing 8 carbon atoms.

In a particularly useful aspect the invention provides a process for recovering para-xylene from a fluid mixture of aromatic compounds comprising: (a) withdrawing from a perm-selective membrane device a first fluid stream having an enriched content of para-xylene compared to that of a second effluent stream which streams are derived by selective permeation of at least one aromatic compound from a fluid mixture of para-xylene with other aromatic compounds; (b) distributing all or portion of the first stream withdrawn from the membrane device into para-xylene concentration unit to extract therefrom a purified product having an enriched content of the para-xylene compared to that of first stream, and a reject stream as mother liquor product; and (c) contacting all or portion of the para-xylene-depleted second stream withdrawn from the membrane device with a suitable isomerization catalyst under conditions of temperature, pressure, and time sufficient to produce an isomerate having an enriched para-xylene content compared to that of the second stream.

Depending on the separations required, processes according to the invention provide a process for recovering para-xylene from a fluid mixture of aromatic compounds comprising: withdrawing from a membrane device a first fluid stream having an enriched content of para-xylene compared to that of a second effluent stream which streams are derived from a fluid mixture of para-xylene with other aromatic compounds by perm-selective means utilizing membranes comprising at least one polymeric material; distributing all or portion of the first stream withdrawn from the membrane device into para-xylene concentration unit to extract therefrom a purified product having an enriched content of the para-xylene compared to that of first stream, and a reject stream as mother liquor product; and contacting all or portion of the reject stream with a suitable isomerization catalyst under conditions of temperature, pressure, and time sufficient to produce an isomerate having an enriched para-xylene content compared to that of the reject stream.

This invention is particularly useful towards separations involving organic compounds, in particular compounds which are difficult to separate by conventional means such as fractional distillation alone. Typically, these include organic compounds are chemically related as for example substituted aromatic compounds of similar carbon number.

For a more complete understanding of the present invention, reference should now be made to the embodiments illustrated in greater detail in the accompanying drawing and described below by way of examples of the invention.

BRIEF DESCRIPTION OF THE DRAWINGS

The invention is hereinafter described in detail with reference to the accompanying drawings which are schematic flow diagrams depicting aspects of the present invention for recovering para-xylene from a fluid mixture by means of selective permeation of at least one aromatic compound from a fluid mixture of para-xylene with other aromatic compounds; and concentration to extract purified product.

GENERAL DESCRIPTION

Figure 1:
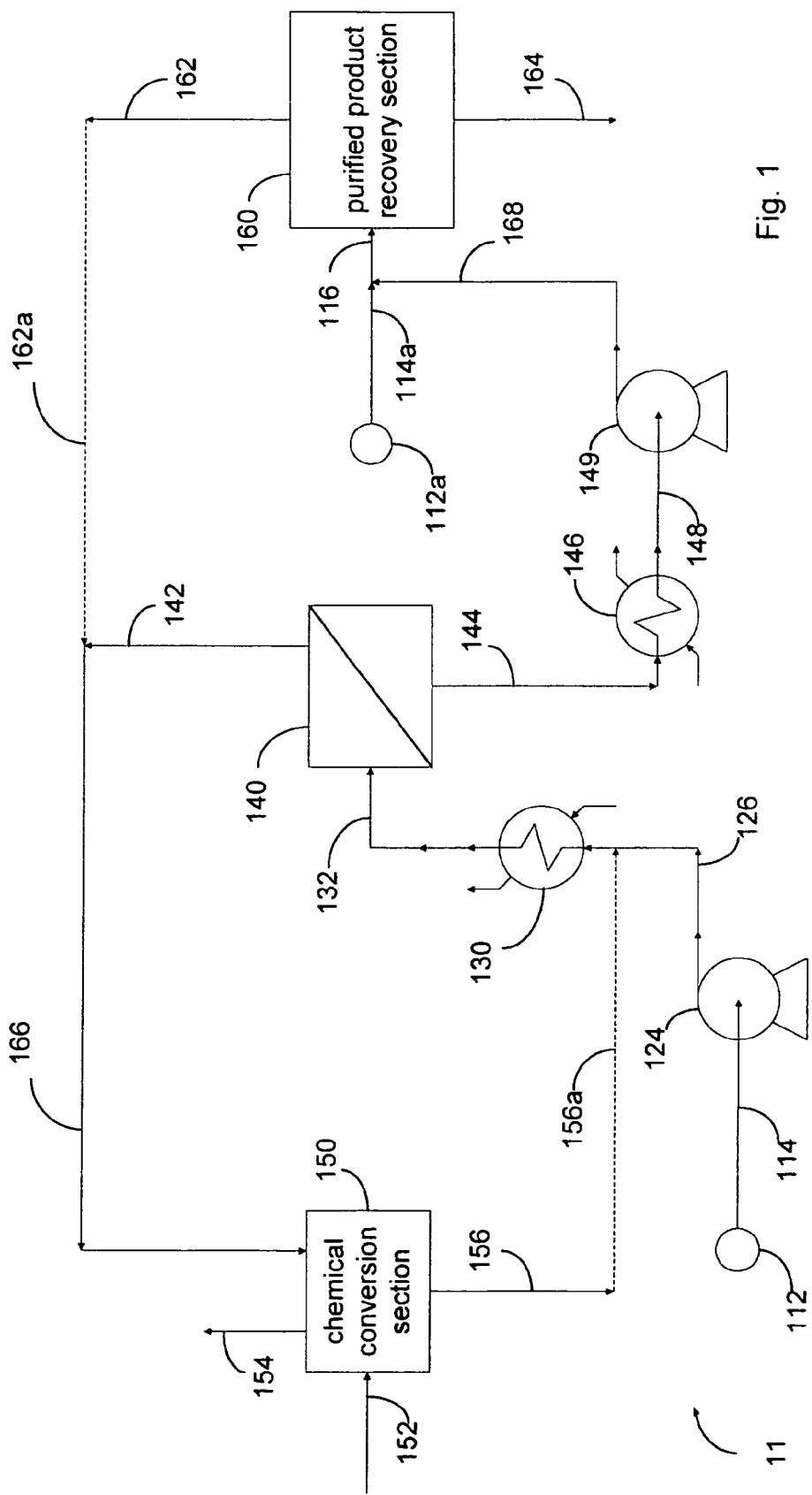
FIG. 1 is schematic drawing showing an embodiment of the present invention in which selective permeation is carried out using perm-selective membranes comprising at least one polymeric material to provide a permeate containing stream having an enriched content of para-xylene.

Any polymeric membrane which under a suitable differential of a driving force exhibits a permeability and other characteristics suitable for the desired separations may be used. For example, membrane devices for separations according to the invention may utilize a plurality of perm-selective membranes which under a suitable differential of a driving force exhibit a permeability of at least 0.1 Barrer for at least one of the isomers of xylene or ethylbenzene. Suitable membranes may take the form of a homogeneous membrane, a composite membrane or an asymmetric membrane which, for example may incorporate a gel, a solid, or a liquid layer.

Membranes useful for the separation of to $C_8$ aromatics in accordance with the invention include polymeric membrane systems. In such membrane systems, molecules permeate through the membrane. During permeation across the polymeric membrane, different molecules are separated due to the differences of their diffusivity and solubility within the membrane matrix. Not only does molecular size influence the transport rate of each species through the matrix but also the chemical nature of both the permeating molecules and the polymer phase itself.

Advances in polymeric membranes make them attractive candidates for separation of aromatic compounds since they do not depend on easily poisoned metal complexes to achieve the separation. For example, several polymeric materials that could be used for the separation of a mixture of aromatic compounds are described in a recent Patent Application Publication number US 2003/0140789 A1 the disclosure of which is incorporated herein by reference in its entirety. Suitable polymers useable as either the membrane material or the porous support include substituted or unsubstituted polymers, for example members of the group consisting of polysulfones, polycarbonates, polyamides and polyimides, including aryl polyamides and aryl polyimides, polyethers, polyetherimides, polyetherketones, polyethersulfones, poly(arylene oxides) such as poly(phenylene oxide) and poly(xylene oxide), poly(esteramide-diisocyanate), polyurethanes, polyesters (including polyarylates), such as polyethylene terephthalate, poly(alkyl methacrylates), poly(acrylates) and poly(phenylene terephthalate), polypyrrolones, polysulfides, polyallyls, poly(benzobenzimidazole), polyhydrazides, polyoxadiazoles, polytriazoles, poly(benzimidazole), polycarbodiimides, and polyphosphazines, and interpolymers, including block interpolymers containing repeating units from the above such as terpolymers of acrylonitrile-vinyl bromide-sodium salt of para-sulfophenylmethallyl ethers; and grafts and blends containing any of the foregoing. Typical substituents providing substituted polymers include halogens such as fluorine, chlorine and bromine; hydroxyl groups; lower alkyl groups;

lower alkoxy groups; monocyclic aryl; lower acyl groups and the like. Polymers beneficially useful in the hollow fiber membranes for the present invention include polyimides, polyethersulfones, polyetherimides and polysulfones, including polyimides, polyetherimides, and polysulfones made using analogs of 6FDA. Particularly useful are polyimides that comprise polyimides or polyetherimides made using 6FDA.

Advantageously the hollow fiber polymer membrane is a composite material comprising an effective skin layer and a porous support. The porous support material can be the same or different polymer as the membrane. Generally the porous support is an inexpensive porous polymer. In a composite hollow fiber polymer membrane the porous support layer can be either the inside layer or the outside layer. Typically the porous support layer is the inside layer in this embodiment and the "skin" layer is on the outside of the hollow fiber.

Composite membrane materials are described in copending U.S. patent applications Ser. Nos. 09/834,857 and 09/834,808 which are incorporated herein in their entirety. A Patent that discusses composite membranes is example U.S. Pat. No. 4,925,459 which is also incorporated herein by reference in its entirety.

High permeability and selectivity of hollow fiber membranes, beneficial for practice of the present invention, depends at least in part upon control of the molecular weight of the polymer material. Control of molecular weight is needed to form hollow fiber membranes that are not too brittle and exhibit an effective skin layer. Generally for processes of the present invention, the average polymer molecular weight is between about 20,000 and about 200,000, typically between about 40,000 and about 160,000, and depending upon the separation desired between about 60,000 and about 120,000 for best results. It is thought that the molecular weight of the polymer should be above, perhaps well above, the entanglement molecular of the polymer in order to achieve a material that has high strength and is not brittle.

Particularly suitable in processes of the present invention is a class of perm-selective membranes which comprise: (i) a polymeric material, and (ii) incorporated therein a plurality of granules comprising at least one natural and/or synthetic crystalline aluminosilicate thereby enhancing the performance of the membrane for the desired separation. Structures of crystalline aluminosilicate are best identified by their structure type code as assigned by the IZA Structure Commission following the rules set up by the IUPAC Commission on Zeolite Nomenclature. Each unique framework topology is designated by a structure type code consisting of 3 capital letters. Advantageously the aluminosilicate exhibits a crystalline structure identified by the following types: AEL, AFO, AHT, BEA, CGF, DAC, EPI, EUO, FER, HEU, LAU, MEL, MFI, MFS, MTT, NES, PAR, SFF, STF, STI, TER, and TON.

Examples of specific useful zeolites include but are not limited to ZSM-5, ZSM-11, ZSM-22, ZSM-23, ZSM-35, ZSM-48, ZSM-57, SUZ-4, SSZ-23; SSZ-25, SSZ-28, SSZ-32, SSZ-36, NU-87, and silicalite. ZSM-5 is described in example U.S. Pat. No. Re. 29,948 (of original U.S. Pat. No. 3,702,886). ZSM-11 is described in U.S. Pat. No. 3,709,979. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is described in U.S. Pat. No. 4,585,747. SUZ-4 is described in EP Application Number 353,915. SSZ-23 is described in U.S. Pat. No. 4,859,422. SSZ-25 is described in U.S. Pat. Nos. 4,827,667 and 5,202,014. SSZ-28 is described in U.S. Pat. No. 5,200,377. SSZ-32 is described in U.S. Pat. No. 5,053,373. SSZ-36 is described in U.S. Ser. No. 60/034,252.

Another suitable class of perm-selective membranes comprise: (i) a polymeric material, and (ii) incorporated therein a plurality of granules comprising at least one natural and/or synthetic silicalite. Silicalite is a hydrophobic crystalline silica-based molecular sieve which has been developed and patented (see U.S. Pat. No. 4,061,724) to Gross et al.). A detailed discussion of silicalite may be found in the article "Silicalite, A New Hydrophobic Crystalline Silica Molecular Sieve"; Nature, Vol. 271, Feb. 9, 1978, incorporated herein by reference. The entire contents of all these patents and patent applications are incorporated herein by reference. Other useful granules may include a cyclodextrin.

Cation modification of the crystalline structure can be used to affect the separation characteristics of the membrane. Such cation modification includes ion exchange where sodium or potassium ions in the structure are replaced with other ions such as barium, calcium, cesium, or any other selected exchangeable ion. This can be done to adjust the adsorption characteristics of the membrane thus increasing the selectivity.

The average size of the granules useful in the present invention is generally less than 0.5 microns, and less than 0.2 microns for best results. Smaller size facilitates bonding between the granules and the polymer. Typically, the size is controlled by synthesis. Prior to membrane formation, the granules may be treated to permit improved bonding between the outer surface of the granules and the polymer. For example, by mixing the sieve in an ethanol/water mixture containing the silane compound for a period of time (a few minutes up to a few hours), then recovering the treated sieve and washing with ethanol to remove excess silane.

Yet another suitable class of perm-selective membranes comprise: (i) a polymeric material, and (ii) incorporated therein a plurality of granules comprising borosilicate, silico-aluminophosphate, aluminophosphate, and other zeolite-like molecular sieves. These zeolite-like molecular sieves can have structures similar to the aluminosilicate zeolites discussed above.

A useful class of membranes for separation embodiments of is a type of composite membranes which comprise a microporous support, onto which the perm-selective layer is deposited as an ultra-thin coating. Composite membranes are beneficial when a rubbery polymer is used as the perm-selective material. Another useful class is asymmetric membrane in which a thin, dense skin of the asymmetric membrane is the perm-selective layer. Both composite and asymmetric membranes are known in the art. The form in which the membranes are used in the invention is not critical. They may be used, for example, as flat sheets or discs, coated hollow fibers, spiral-wound modules, or any other convenient form.

Suitable types of membrane devices include the hollow-fine fibers, capillary fibers, spiral-wound, plate-and-frame, and tubular types. The choice of the most suitable membrane module type for a particular membrane separation must balance a number of factors. The principal module design parameters that enter into the decision are limitation to specific types of membrane material, suitability for high-pressure operation, permeate-side pressure drop, concentration polarization fouling control, permeability of an optional sweep stream, and last but not least costs of manufacture.

Hollow-fiber membrane modules are used in two basic geometries. One type is the shell-side feed design, which has been used in hydrogen separation systems and in reverse osmosis systems. In such a module, a loop or a closed bundle of fibers is contained in a pressure vessel. The system is pressurized from the shell side; permeate passes through the fiber wall and exits through the open fiber ends. This design is easy to make and allows very large membrane areas to be contained in an economical system. Because the fiber wall must support considerable hydrostatic pressure, the fibers usually have small diameters and thick walls, e.g. 100 µm to 200 µm outer diameter, and typically an inner diameter of about one-half the outer diameter.

A second type of hollow-fiber module is the bore-side feed type. The fibers in this type of unit are open at both ends, and the feed fluid is circulated through the bore of the fibers. To minimize pressure drop inside the fibers, the diameters are usually larger than those of the fine fibers used in the shell-side feed system and are generally made by solution spinning. These so-called capillary fibers are used in ultra-filtration, pervaporation, and some low- to medium-pressure gas applications.

Concentration polarization is well controlled in bore-side feed modules. The feed solution passes directly across the active surface of the membrane, and no stagnant dead spaces are produced. This is far from the case in shell-side feed modules in which flow channeling and stagnant areas between fibers, which cause significant concentration polarization problems, are difficult to avoid. Any suspended particulate matter in the feed solution is easily trapped in these stagnant areas, leading to irreversible fouling of the membrane. Baffles to direct the feed flow have been tried, but are not widely used. A more common method of minimizing concentration polarization is to direct the feed flow normal to the direction of the hollow fibers. This produces a cross-flow module with relatively good flow distribution across the fiber surface. Several membrane modules may be connected in series, so high feed solution velocities can be used. A number of variants on this basic design have been described, for example U.S. Pat. No. 3,536,611 in the name of Fillip et al., U.S. Pat. No. 5,169,530 in the name of Sticker et al., U.S. Pat. No. 5,352,361 in the name of Parsed et al., and U.S. Pat. No. 5,470,469 in the name of Beckman which are incorporated herein by reference each in its entirety. The greatest single advantage of hollow-fiber modules is the ability to pack a very large membrane area into a single module.

Sources of xylenes in substantial quantities include certain virgin and reformed petroleum naphthas and coke oven light oils. When removed from typical petroleum-derived feedstocks, para-xylene is found in mixtures with other $C_8$ aromatics; namely: meta-xylene, ortho-xylene, and ethylbenzene. Generally, processes of the invention recover a very pure isomer of xylene from distillate fractions containing the xylene isomers, ethylbenzene, and paraffins.

While many sources of $C_8$ aromatics may be fed to the process, in a typical $C_8$ fraction from a naphtha reformer and aromatics recovery unit the mixture contains approximately 15 percent ethylbenzene, 22 percent para-xylene, 50 percent meta-xylene and 22 percent ortho-xylene and varying amounts of unsaturated, linear and cyclic hydrocarbons.

For example, one method of producing a para-xylene product from a $C_8$ aromatic mixture is to first pass the $C_8$ mixture to a xylene column to remove heavies, for example, $C_8$+ hydrocarbons. The three isomers of xylene have an equilibrium ratios of approximately 1:2:1 for para:meta: ortho, and depending on the source, ethylbenzene can compose from 0 to about 20 percent by weight of a $C_8$ aromatics mixture leaving only about 80 to 99 percent xylenes. The overhead stream from the xylene column, containing predominantly para-xylene, meta-xylene and ethylbenzene is passed to a perm-selective membrane device to obtain a first fluid stream having an enriched content of para-xylene which is thereafter concentrated by fractional crystallization and/or sorption.

Particularly useful methods of para-xylene concentration according to the present invention include fractional crystallization. Suitable fractional crystallization units operate in manors described in, for example, U.S. Pat. No. 3,177,265 in the name of Gerard CLammers, U.S. Pat. No. 3,462,509 in the name of Thorpe Dresser, Stanley Ohiswager and Robert Edlson, U.S. Pat. No. 3,720,647 in the name of Horst Gelbe and Karl Schmid, U.S. Pat. No. 3,723,558 in the name of Friedrich Kramer, U.S. Pat. No. 5,004,860 in the name of John S. Hansen and William A. Waranius, U.S. Pat. No. 5,498,822 in the name of William D. Eccli and Alexander D. S. Fremuth, U.S. Pat. No. 5,866,740 in the name of Paul Mikitenko and Gerard Paul Hotier, U.S. Pat. No. 6,111,161 in the name of Stuart R. MacPherson and Paul Mikitenko, U.S. Pat. No. 6,147,272 in the name of Paul Mikitenko and Stuart R. MacPherson, and U.S. Pat. No. 6,194,609 in the name of Keneth J. Abrams, Thomas M. Bartos and Debra J. Streich, which are incorporated herein by reference in their entirety.

Fractional crystallization that takes advantage of the fact that for most xylene mixtures the melting point of paraxylene is higher than the other xylene isomers and crystallizes first. For example, para-xylene crystallizes at 13.3° C., meta-xylene at negative 47.9° C. and ortho-xylene negative 25.2° C. In the physical system of the three xylene isomers, there are two binary eutectics of importance, the paraxylene/meta-xylene and the para-xylene/ortho-xylene. As the para-xylene is crystallized from the mixture, the remaining mixture (mother liquor) composition approaches one of these eutectic binaries depending on the starting composition of the mixture. In practice according to the invention, para-xylene is crystallized so that the binary is only approached but not reached to avoid contaminating the crystal body with a mixture of crystals. This represents the eutectic limit to recovering para-xylene by crystallization. The crystallization unit produces a mother liquor which is beneficially recycled to the isomerization unit where the composition of the mother liquor is restored to the approximate concentration of the initial $C_8$ aromatic feedstock to provide a source of additional para-xylene.

In a two stage crystallizer, an equilibrium $C_8$ aromatic feed is cooled to about negative 35° to about negative 40° C. and mixed with second stage filtrate and then crystallized in a number of crystallizers in series, each crystallizer cooling the feed further, the coldest of which runs typically at about negative 62° to about 68° C. The slurry solids and liquor, i.e. mother liquor, are separated by centrifuge. In the first stage, the solids become a wet cake with voids filled by the liquid containing only about 8 to about 12 percent by weight para-xylene. This low para-xylene liquid contaminates the crystals by about 5 to about 20 percent, depending on the drying efficiency of the liquid-solid separation means and prevents the para-xylene concentration from achieving the required 99.5+ percent purity. The remaining liquid is discharged as reject filtrate. This wet cake is either fully or partially melted and recrystallized or washed to remove the contaminants to achieve the required high para-xylene purity.

The second stage re-crystallizes the first stage product and filtrate para-xylene from the second stage recycle filtrate out of solution. The resulting slurry of crystals and mother liquor is centrifuged. The wet para-xylene crystals cake goes to the wash step, the remaining liquid is recycled filtrate. A controlled amount of the recycle filtrate is used to dilute the first stage product in order to control the slurry solids loading in the crystallizer. Typical centrifuges separate a slurry mixture containing no more than 35 to 45 percent by weight solids. The second stage crystallizer operates in range of temperature from about negative 18° up to about 5° C. and thus requires and processes a much smaller stream than the first stage and thus requires much less refrigeration.

The second stage cake voids are filled with liquid that is already rich in para-xylene, typically about 60 to about 75 percent by weight and thus washing the crystals with product para-xylene can achieve a feed purity in the order of 99.8 para-xylene.

The composition of a suitable $C_8$ aromatic stream will vary depending on its source, but the total ortho-xylene and para-xylene isomer content will be less than about 45 percent. However, the integrated perm-selective separations and purified product recovery operations alone will not fully utilize the $C_8$ aromatic feedstock. Under these circumstances, in one aspect of the invention, chemical conversions such as isomerization are useful. After depleting the $C_8$ aromatic feedstock of the valuable para-xylene isomer, the depleted stream is advantageously sent to an isomerization unit. In the isomerization unit, an equilibrium xylene isomer ratio is established, thereby producing the desired isomers from the undesirable ones.

There are two generally useful processes for the production of para-xylene from a mixture of $C_8$ aromatics. Each process includes a catalyst section containing one or more catalysts for conversion of a portion of ethylbenzene to benzene, or other products and a catalyst for isomerization of xylenes. Additionally, the process includes distillation towers for removal of components boiling above and below that of the $C_8$ aromatics, and finally, a section for purification and recovery of the para-xylene product, generally at purities greater than 99.8 percent by weight.

Particularly useful methods of chemical conversions for production of purified para-xylene according to the present invention include catalytic isomerization of xylenes. Suitable isomerization units operate in manors described in, for example, U.S. Pat. No. 3,856,871 in the name of Werner O. Haag and David H. Olson, U.S. Pat. No. 4,101,597 in the name of Lloyd L. Breckenridge, U.S. Pat. Nos. 4,218,573 and 4,236,996 in the name of Samuel A. Tabak and Roger A Morrison, U.S. Pat. No. 4,224,141 in the name of Roger A Morrison and Samuel A. Tabak, U.S. Pat. No. 4,638,105 in the name of Clarence D. Chang and Joseph N Miale, and U.S. Pat. No. 4,899,011 in the name of Yung F Chu, Charles T. Kresge and Rene B. LaPiere, which are incorporated herein by reference in their entirety.

Extraction of high purity para-xylene product from a stream of mixed xylenes and impurities according to one embodiment of the invention comprises the steps of cooling a feed of mixed xylenes and impurities in at least one crystallizer in a fractional crystallization unit to crystallize out para-xylene from the liquid-crystal slurry, separating the liquid component comprising ortho-xylene and meta-xylene and impurities from the solid crystal para-xylene in a separation means, e.g., centrifuge, to obtain high purity para-xylene. Advantageously at least a portion of the reject stream (xylenes and impurities), including melted para-xylene due to work input and/or heat from the environment, is supplied to an isomerization unit where the xylenes are reacted over a catalyst bed, separating para-xylene and mixed xylenes from impurities in a distillation stage and returning the mixed xylenes to the membrane device and subsequently the fractional crystallization unit.

In a particularly advantageous aspect of the invention, para-xylene concentrations in the stream from the membrane device for distribution to the crystallization unit, are high enough that eutectic temperature is not a factor in the operation of the crystallizers of the present invention. This is because cooling to the eutectic temperature is not required to get high para-xylene recovery rates. Beneficially, para-xylene purity of at least 99.5 percent by weigh can be achieved in a single temperature stage because of the high concentration of para-xylene in the crystallizer feed and the high para-xylene concentration in the mother liquor.

In this aspect of the present invention a single temperature stage crystallizer can employ a wash using only para-xylene product. No other type of wash, such as toluene, is needed to produce 99.8 percent para-xylene purity. Thus para-xylene product of the present invention requires no further processing.

Where the invention includes a single stage crystallization to recover para-xylene from a stream rich in para-xylene, operation of the fractional crystallization unit comprises: contacting the stream rich in para-xylene in a single temperature crystallization stage at a temperature in the range of from about negative 30° C. to about 10° C.; withdrawing a slurry comprising para-xylene crystals from the single temperature crystallization stage; forming a cake of crystals with a separation means, for example a centrifuge separation means, a filter and/or hydrocyclone, and washing the cake with para-xylene. Advantageously a portion of the reject stream from the separation means is recycled to the single temperature crystallization stage. The washed cake is melted to form purified para-xylene product.

Another class of particularly useful methods of para-xylene concentration according to the present invention include selective sorption methods, such as liquid-phase adsorption chromatography, or simulated moving bed adsorption (SMBA), are described in, e.g. U.S. Pat. No. 2,985,589 in the name of Donald B Broughton and Clarence G. Gerhold, U.S. Pat. No. 3,732,325 in the name of Joe M. Pharis, Donald B Broughton and Robert F Zabransky, U.S. Pat. No. 3,706,812 in the name of Armand J. deRosset and Richard W. Neuzil, U.S. Pat. Nos. 3,626,020 and 3,696,107 in the name of Richard W. Neusil, U.S. Pat. No. 3,729,523 in the name of Philip Grandio, Jr. and Paul T. Allen, U.S. Pat. No. 4,381,419 in the name of Roger Wylie, U.S. Pat. No. 4,402,832 in the name of Clarence G. Gerhold, U.S. Pat. No. 4,886,929 in the name of Richard W. Neuzil and George J. Antos, and U.S. Pat. No. 5,329,060 in the name of John D. Swift, which are incorporated herein by reference in their entirety.

Selective sorption operations have the following characteristics. In order to obtain high purity and high recovery, the adsorbent column is generally divided into a plurality of beds. The product recovery is obtained by desorbing the $C_8$ aromatics with a solvent, generally toluene or para-diethylbenzene. The desorbent solvent, typically separated from the desired products by fractional distillation, is recycled internally in the purified product recovery section.

Advantageously, a selective sorption operation is carried out in accordance with the invention using an adsorbent that is selective for the adsorption of meta-xylene and ortho-xylene or, in the alternative, selective for the adsorption of para-xylene. In the case where the sorbent is selective for the adsorption of meta- and ortho-xylene, an extract rich in meta-xylene and ortho-xylene and depleted in para-xylene is rejected to the isomerization zone and a para-xylene-enriched raffinate is sent to the crystallization zone for recovery of para-xylene. In the case where the sorbent is selective for the adsorption of para-xylene, a raffinate rich in meta-xylene and ortho-xylene and depleted in para-xylene is rejected to the isomerization zone and a para-xylene-enriched extract is sent to the crystallization zone for recovery of para-xylene. Beneficially, at least a portion of a reject stream that contains the lowest para-xylene concentration is treated in an isomerization step.

Typically, the sorbents used in processes of the present invention are molecular sieves that can comprise both the natural and synthetic aluminosilicates. A crystalline aluminosilicate encompassed by the present invention for use as an adsorbent includes aluminosilicate cage structures in which alumina and silica tetrahedra are intimately connected with each other in an open three-dimensional crystalline network. The tetrahedra are cross-linked by the sharing of oxygen atoms with spaces between the tetrahedra occupied by water molecules prior to partial or total dehydration of this zeolite. The dehydration results with crystals interlaced with channels having molecular dimensions. Thus, the crystalline aluminosilicates are often referred to as molecular sieves.

Crystalline aluminosilicates which find use as the adsorbent in the process of the present invention possess relatively well defined pore structures. The exact type of aluminosilicate is generally referred to by the particular silica alumina ratio. Faujasites are commonly represented as being closely related to the type X and type Y aluminosilicates and are defined by the varying silica to alumina ratios. Type X is described in U.S. Pat. No. 2,882,244 and type Y is described in U.S. Pat. No. 3,130,007 which are incorporated herein by reference in their entirety.

Adsorbents contemplated herein include not only the sodium form of the type Y zeolite but also crystalline materials contained from such a zeolite by partial or complete replacement of the sodium cations with other individual cations. Similarly, the type X zeolite also ion exchanges and is contemplated for use as an adsorbent process of this invention.

In accordance with the present invention, the para-xylene-depleted stream is beneficially contacted with an isomerization catalyst in an isomerization zone at isomerization conditions sufficient to produce an isomerate comprising an equilibrium xylene mixture. Useful isomerization catalysts can be any suitable isomerization catalyst known to those skilled in the art. Such catalyst will typically comprise an acidic inorganic oxide support which has incorporated at least one metallic component.

Where an inorganic oxide binder is utilized in formation of the isomerization catalyst, the binder typically is a porous, adsorptive, high surface area support having a surface area of from about 25 $m^2/g$ to about 500 $m^2/g$, uniform in composition and relatively refractory to the conditions utilized in the isomerization process of the present invention. Examples of suitable binders include alumina, silica, silica-alumina, attapulgus clay, diatomaceous earth, Fuller's earth, kaolin, kieselguhr, and any mixtures thereof. Generally binder is a form of alumina, e.g., the crystalline aluminas known as beta, and theta, and most often gamma alumina. Particularly useful binders have an apparent bulk density of from about 0.3 g/cc to about 0.8 g/cc and surface area characteristics such that the average pore diameter is about 20 to about 300 Angstroms and the pore volume is about 0.1 cc/g to about 1 cc/g.

In an aspect of the invention, the metallic component of the isomerization catalyst, is advantageously selected from Group VI of the Periodic Table, particularly the group comprising molybdenum and tungsten. The metallic Group VIIIA component of the isomerization catalyst may exist within the final catalyst as an oxide, sulfide, or as an elemental metal, or as any combination thereof. The metallic Group VIB component of the isomerization catalyst generally comprises from about 0.1 to about 10 percent by weight of the final catalyst, and from about 2 to about 5 percent by weight for best results.

In another aspect of the invention, the metallic component of the isomerization catalyst, is beneficially selected from Group VIIIA metals, particularly the group comprising cobalt, palladium, rhodium, ruthenium, and iridium, and in particular nickel and platinum. The metallic Group VIIIA component of the isomerization catalyst may exist within the final catalyst as an oxide, sulfide, or as an elemental metal, or as any combination thereof. The metallic Group VIIIA component of the isomerization catalyst generally comprises from about 0.01 to about 2 percent by weight of the final catalyst, and from about 0.05 to about 1.0 percent by weight for best results.

In an isomerization operation according to the invention the catalyst can be arranged in a fixed-bed system, a moving bed system, a fluidized bed system, or in a batch-type operation. In view of the danger of catalyst attrition loss and of operational advantages, generally it is used in a fixed-bed system. In this system, a hydrogen gas and the para-xylene depleted stream are preheated by suitable heating means to the desired reaction temperature and then passed into an isomerization zone containing a fixed bed of catalyst. The isomerization conversion zone may be one or more separate reactors with suitable means therebetween to ensure that the desired isomerization temperature is maintained at the entrance to each zone. Reactants may be contacted with the catalyst in the upward-flow, downward-flow, or radial-flow fashion. Further, the reactants may be in liquid phase, vapor phase, or vapor/liquid phase when contacting the catalyst.

Suitable isomerization conditions include temperatures in a range of from about 0° C. to about 600° C., but typically are in a range of from about 350° C. to about 500° C., pressures are in a range of from about 1 to 100 atmospheres, but typically are in a range of from about 2 to about 30 atmospheres, a hydrogen to hydrocarbon mole ratio of from about 0.5:1 to about 15:1, and a liquid hourly space velocity of about 0.5 $hr^{-1}$ to about 30 $hr^{-1}$.

In accordance with the present invention, at least a portion of the paraxylene-enriched stream is passed to the perm-selective membrane device. Advantageously, the eutectic limit of para-xylene crystallization is overcome by enriching the concentration of para-xylene of the crystallization feed. A para-xylene-depleted reject stream is passed to an isomerization zone to re-equilibrate the xylene mixture, thereby producing additional para-xylene. A para-xylene-enriched stream withdrawn from the perm-selective membrane device is passed to a crystallization zone to produce high purity para-xylene. The result is an increase in the overall para-xylene recovery.

DESCRIPTION OF THE PREFERRED EMBODIMENTS

Referring to FIG. 1 which is schematic flow diagram depicting preferred aspects of an integrated process and apparatus of the present invention using perm-selective membranes comprising at least one polymeric material to provide a permeate containing stream having an enriched in at least one compound of the feed mixture relative to the non-permeate, for example para-xylene.

A first feed stream, for example a mixture of the $C_8$ aromatic compounds, is supplied form source 112 into exchanger 130 of integrated apparatus 11 through conduit 114, pump 124 and manifold 126. An effluent stream at suitable process conditions is withdrawn from exchanger 130 through manifold 132 and distributed into membrane device 140 which typically includes a plurality of perm-selective polymer membranes whereby permeate and non-permeate mixtures having different compositions are derived from the feed.

A stream of permeate which is enriched in at least one compound of the feed mixture relative to the non-permeate, is withdrawn form membrane device 140 through conduit 144, and transferred into an integrated purified product recovery section 160 through exchanger 146 conduit 148, conduit 168, and manifold 116 by means of pump 149. For example where the first feed stream comprises a mixture of the $C_8$ aromatic compounds and the permeate is enriched in at least para-xylene, recovery comprises a para-xylene concentration unit which advantageously utilizes fractional crystallization and/or selective sorption. Purified product is withdrawn from recovery section 160 through conduit 164. A stream depleted in the desired product is withdrawn through conduit 162.

An alternative or supplemental stream, enriched in at least para-xylene, is optionally supplied from source 112a into manifold 116 through conduit 114a.

A stream of non-permeate which is depleted in at least one compound of the feed mixture relative to the permeate, is withdrawn form membrane device 140, and transferred into an integrated chemical conversion section 150 through conduit 142 and manifold 166. Advantageously all or a portion of the stream depleted in the desired product withdrawn from the purified product recovery section through conduit 162 is also transferred into section 150, for example through conduit 162, conduit 162a and manifold 166. Chemical conversions of at least a portion of the stream generally include isomerization reactions to thereby establish an equilibrium mixture. Another reactant, such as hydrogen, may be supplied to section 150 through conduit 152 and excess reactants and/or co-products are withdrawn from section 150 through conduit 154. A stream comprising at least a portion of the conversion products, for example an equilibrium mixture of aromatic hydrocarbons having about 8 carbon atoms, is withdrawn from section 150 through conduit 156. Where the stream of conversion products is enriched in a desired compound in the permeate, stream withdrawn through conduit 156 is advantageously directed into membrane device 140 through conduit 156, conduit 156a and manifold 126.

A para-xylene enriched stream from the chemical conversion section typically contains about 22 percent para-xylene in an equilibrium admixture with the other $C_8$ aromatic compounds. Due to formation of a eutectic composition during crystallization, however, without a perm-selective separation device, recovery of para-xylene product of 99.8 percent purity from the 22 percent composition is restricted to about 65 percent. An Aspen computer program was used to simulate one embodiment of the invention depicted in FIG. 1. A membrane device using perm-selective membrane which exhibits a para-xylene selectivity of 10, beneficially increased the para-xylene concentration of crystallization feed to 50 percent. Amount of crystallization feed decreased by about two thirds, and the para-xylene lean reject stream is decreased by about 20 percent. Thus the para-xylene process using perm-selective membranes according to the invention provides an economically significant increase in yield of purified para-xylene.

Figure 2:
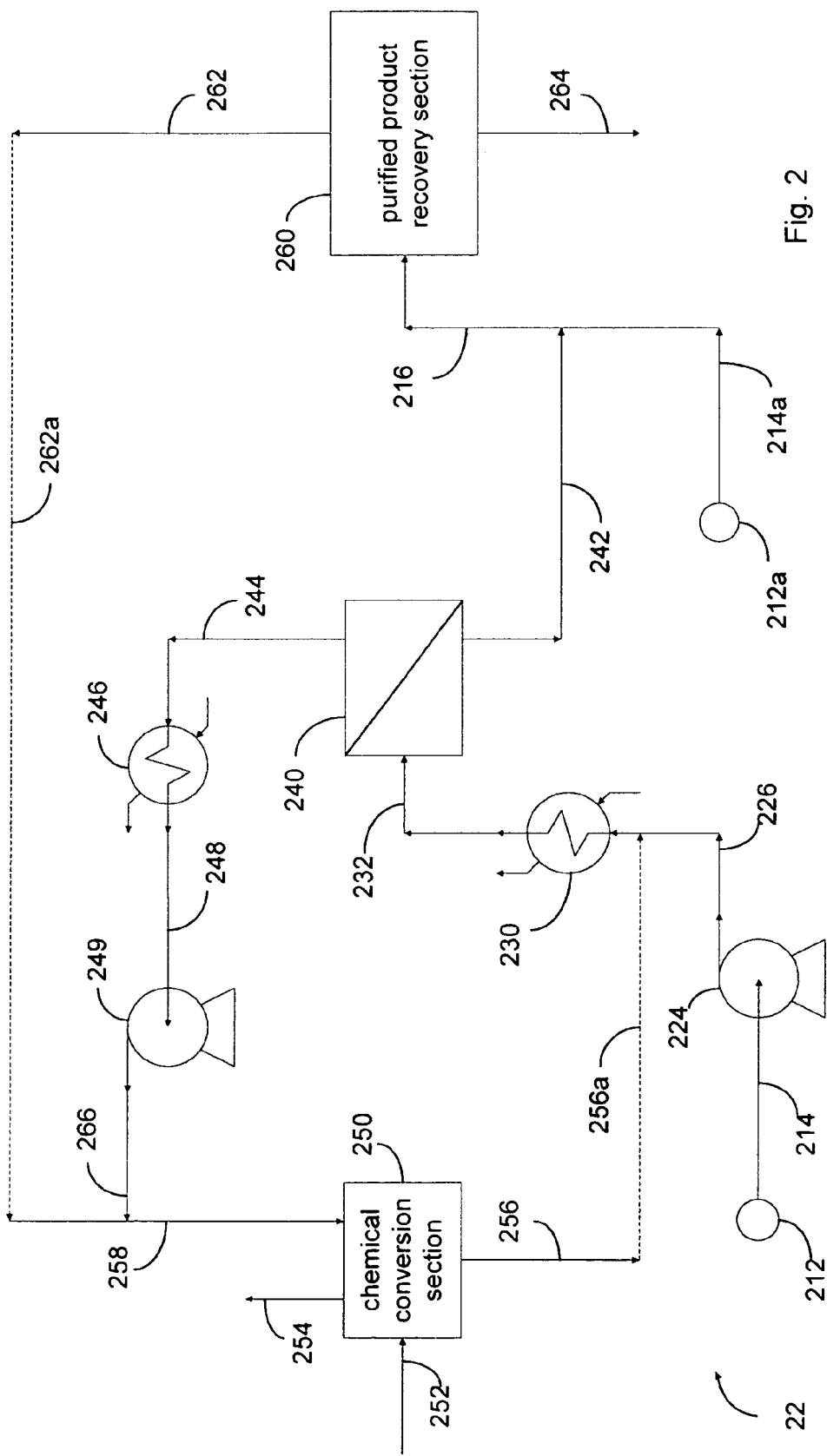
FIG. 2 is schematic drawing showing an embodiment of the present invention in which selective permeation is carried out using perm-selective membranes comprising at least one polymeric material to enrich the para-xylene content of the non-permeate containing stream.

Referring to FIG. 2 which is schematic flow diagram depicting preferred aspects of an integrated process and apparatus 22 of the present invention using perm-selective membranes comprising at least one polymeric material to enrich the para-xylene content of the non-permeate containing stream.

A first feed stream, for example a mixture of the $C_8$ aromatic compounds, is supplied form source 212 into exchanger 230 through conduit 214, pump 224 and manifold 226. An effluent stream at suitable process conditions is withdrawn from exchanger 230 through manifold 232 and distributed into membrane device 240 which typically includes a plurality of perm-selective polymer membranes whereby permeate and non-permeate mixtures having different compositions are derived from the feed.

A stream of non-permeate which is enriched in at least one compound of the feed mixture relative to the permeate, is withdrawn form membrane device 240 through conduit 242, and transferred through manifold 216 into an integrated purified product recovery section 260. For example where the first feed stream comprises a mixture of the $C_8$ aromatic compounds and the non-permeate is enriched in at least para-xylene, recovery comprises a para-xylene concentration unit which advantageously utilizes fractional crystallization and/or selective sorption. Purified product is withdrawn from recovery section 260 through conduit 264. A stream depleted in the desired product is withdrawn through conduit 262 and manifold 258. Optionally a supplemental stream from source 212a, enriched in at least para-xylene, is also transferred into an integrated purified product recovery section 260 through conduit 214a and manifold 258.

A stream of permeate which is depleted in at least one compound of the feed mixture relative to the permeate, is withdrawn form membrane device 240 through conduit 244, and transferred through exchanger 246 conduit 248, and by means of pump 254 through conduit 266 and manifold 258 into an integrated chemical conversion section 250. A stream depleted in the desired para-xylene product is withdrawn from the purified product recovery section through conduit 262. Advantageously all or a portion of the depleted stream is transferred into chemical conversion section 250, for example through conduit 262a and manifold 254. Another reactant, such as hydrogen, may be supplied to section 250 through conduit 252 and excess reactants and/or co-products are withdrawn from section 250 through conduit 254. A stream comprising at least a portion of the conversion products, for example an equilibrium mixture of aromatic hydrocarbons having about 8 carbon atoms, is withdrawn from section 250 through conduit 256. Where the stream of conversion products is enriched in a desired compound in the permeate, stream withdrawn through conduit 256 is advantageously directed into membrane device 240 through conduit 256, conduit 256a and manifold 226.

That which is claimed is:

1. A process for recovering para-xylene from a fluid mixture of aromatic compounds, including at least one other isomer of xylene and ethylbenzene, which process comprises:

(1-A) withdrawing from a perm-selective polymeric membrane device a first fluid stream having an enriched content of para-xylene compared to that of a second effluent stream which streams are derived by selective permeation of at least one aromatic compound from a fluid mixture of para-xylene with other aromatic compounds containing 8 carbon atoms, utilizing perm-selective membranes comprising at least one poly(amide)imide material having an average molecular weight between 20,000 and 200,000, which membranes exhibit a permeability of at least 0.1 Barrer for at least one of the isomers of xylene or ethylbenzene; and (1-B) distributing all or portion of the first stream withdrawn from the membrane device into para-xylene concentration unit to extract therefrom a purified product having an enriched content of the para-xylene compared to that of first stream, and a reject stream lean in at least para-xylene.

2. The process according to claim 1 wherein the membrane device utilizes a plurality of perm-selective membranes.

3. The process according to claim 2 wherein the reject stream comprises ethylbenzene; and the process further comprises;

passing at least a portion of the reject stream to an ethylbenzene catalytic conversion and/or xylene isomerization process to produce a stream having an enriched para-xylene content compared to that of the reject stream.

4. The process according to claim 3 wherein the fluid mixture comprises at least a portion of the isomerate.

5. The process according to claim 1 wherein the fluid mixture comprises one or more product of reforming, hydroprocessing, toluene disproportion, a $C_6$ to $C_{10}$ aromatics trans-alkylation, and/or methylation of benzene and/or toluene reactions.

6. The process according to claim 1 wherein the membrane device utilizes a perm-selective membrane comprising at least one cyclodextrin selected from the group consisting of β-cyclodextrin and γ-cyclodextrin, and polymeric material having an average molecular weight between 60,000 and 120,000 selected from the group consisting of, polyimides, and poly(amide)imides.

7. A process for recovering para-xylene from a fluid mixture of aromatic compounds, including at least one other isomer of xylene and ethylbenzene, which process comprises:

(23-A) withdrawing from a membrane device a first fluid stream having an enriched content of para-xylene compared to that of a second effluent stream which streams are derived from a fluid mixture of about 22 percent para-xylene with other aromatic compounds containing 8 carbon atoms, by perm-selective means utilizing membranes comprising at least one poly(amide)imide material having an average molecular weight between 20,000 and 200,000, which membranes exhibit a para-xylene selectivity of 10, and thereby increase the para-xylene concentration in the first fluid stream to a level of 50 percent or more;

(23-B) distributing all or portion of the first stream withdrawn from the membrane device into para-xylene concentration unit to extract therefrom a purified product having an enriched content of the para-xylene compared to that of first stream, and a reject stream as mother liquor product; and (23-C) contacting all or portion of the reject stream with a suitable isomerization catalyst under conditions of temperature, pressure, and time sufficient to produce an isomerate having an enriched para-xylene content compared to that of the reject stream.

8. The process according to claim 7 wherein the membrane device utilizes a perm-selective membrane comprising at least one cyclodextrin and poly(amide)imide material having an average molecular weight between 60,000 and 120,000.

* * * * *